United States Patent
Chun et al.

(10) Patent No.: US 8,025,776 B2
(45) Date of Patent: Sep. 27, 2011

(54) GLASS ELECTROPHORESIS MICROCHIP AND METHOD OF MANUFACTURING THE SAME BY MEMS FABRICATION

(75) Inventors: Myung-Suk Chun, Seoul (KR); Tae Ha Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1000 days.

(21) Appl. No.: 11/926,509

(22) Filed: Oct. 29, 2007

(65) Prior Publication Data

US 2009/0107844 A1 Apr. 30, 2009

(51) Int. Cl.
    *C23C 14/34* (2006.01)
(52) U.S. Cl. .......... 204/192.15; 204/192.12; 216/39; 216/40; 216/41; 216/52; 216/58; 216/63; 216/67; 216/79; 216/80
(58) Field of Classification Search .......... 204/192.12, 204/192.15; 216/39, 40, 41, 52, 58, 63, 67, 216/79, 80
    See application file for complete search history.

(56) References Cited

U.S. PATENT DOCUMENTS

| 6,045,676 | A * | 4/2000 | Mathies et al. | 204/603 |
|---|---|---|---|---|
| 6,143,152 | A * | 11/2000 | Simpson et al. | 204/451 |
| 6,210,986 | B1 * | 4/2001 | Arnold et al. | 438/42 |
| 6,823,693 | B1 * | 11/2004 | Hofmann et al. | 65/59.4 |
| 6,984,015 | B2 * | 1/2006 | Lattuca et al. | 347/20 |
| 2001/0046781 | A1 * | 11/2001 | Nakagawa | 438/725 |
| 2003/0023149 | A1 * | 1/2003 | Montemagno et al. | 600/300 |
| 2003/0127329 | A1 * | 7/2003 | DeVoe et al. | 204/454 |
| 2005/0236357 | A1 * | 10/2005 | Bakkers et al. | 216/2 |
| 2008/0063566 | A1 * | 3/2008 | Matsumoto et al. | 422/68.1 |
| 2009/0053827 | A1 * | 2/2009 | Taylor et al. | 436/501 |

OTHER PUBLICATIONS

Shigeo Suzuki, et al. "High-speed electrophoretic analysis of 1-phenyl-3-methyl-5-pyrazolone derivatives of monosaccharides on a quartz microchip with whole-channel UV detection," 2003 Wiley-VCH Verlag Gmbh & Co., KGaA, Weinheim, Electrophoresis 2003,24, pp. 3828-3833.

Hiroaki Nakanishi, et al. "Fabrication of quartz microchips with optical slit and development of a linear imaging UV detector for microchip electrophoresis systems," Wiley-VCH Verlag Gmbh. 69451 Weinheim, 2001, Electrophoresis 2001, 22, pp. 230-234.

(Continued)

*Primary Examiner* — Rodney McDonald
(74) *Attorney, Agent, or Firm* — Ladas & Parry LLP

(57) ABSTRACT

Embodiments of the present invention may provide a microchip applicable to an electrophoresis employing UV detection and a method of manufacturing the same. The microchip of the present invention has a glass channel plate, which is formed on an upper surface thereof with a loading channel and a separation channel and is provided on the upper surface thereof with an optical slit layer made of silicon except the channel region, and a glass reservoir plate, which is formed with sample solution reservoirs and buffer solution reservoirs. The loading channel and the separation channel are formed on the channel plate by deep reactive ion etching. The sample solution reservoirs and the buffer solution reservoirs are formed in the reservoir plate by sand blasting. The channel plate and the reservoir plate are combined by anodic bonding the optical slit layer and the reservoir plate. Electrodes for sample and electrodes for buffer are deposited by sputtering Pt with a shadow mask after anodic bonding.

8 Claims, 12 Drawing Sheets

OTHER PUBLICATIONS

Feng Xu, et al. "Single-step quantitation of DNA in microchip electrophoresis with linear imaging UV detection and fluorescence detection through comigration with a digest," 2004 Elsevier B. V., Journal of Chromatography A. 1051 (2004), pp. 147-153.

H. Nakanishi, et al, "Studies on $SiO_2$-$SiO_2$ bonding with hydrofluoric acid. Room temperature and low stress bonding technique for MEMS," 2000 Elsevier Science S.A., Sensors and Actuators 79 (2000), pp. 237-244.

* cited by examiner (a)

(b)

GLASS ELECTROPHORESIS MICROCHIP AND METHOD OF MANUFACTURING THE SAME BY MEMS FABRICATION

BACKGROUND

1. Field

The present invention generally relates to a microchip for electrophoresis, and more particularly to a glass microchip, which has an optical slit made from silicon by MEMS fabrication to effectively cut off a stray light. Further, the present invention relates to a method of manufacturing the same.

2. Background

A micro total analysis system (µTAS), which was established along with advancements of nano and bio technologies, became an essential foundation for a bioMEMS technology. An electrophoretic analysis is mainly used in the µTAS. With regard to selecting channels in which a sample is separated, the electrophoretic analysis is recently being changed from one way of using a fused silica capillary to another way of using a lab-on-a-chip, which is manufactured by MEMS fabrication and micromachining technology. Such electrophoretic analysis using a microchip is attracting great attention as an emergent analysis technology. This is due to the treatment of a small amount of samples, a faster analysis, more convenient operation, a high throughput with improved accuracy, etc.

Various samples such as proteins, DNAs, amino acids, cell particles, etc. can be analyzed by using the electrophoresis microchip. The electrophoresis microchip basically utilizes a microfluidics principle. The electrophoresis microchip is provided with a sample loading channel (into and out of which sample solution to be analyzed flows) and a separation channel (into and out of which buffer solution flows), and which is crossed to the sample loading channel. Inlet and outlet reservoirs of the sample solution and the buffer solution are provided with electrodes so that electric fields can be applied to the sample loading channel and the separation channel. While the sample solution flows from the inlet reservoir to the outlet reservoir, a certain amount of sample solution is positioned at an intersection of the sample loading channel and the separation channel by the electric field applied to the sample loading channel. Then, particles dispersed in the sample solution are separated according to the mobility differences by the electric field applied to the separation channel. The dimensions of the channel of the microchip are several tens µm to about 100 µm in width and depth.

Plastics such as polydimethylsiloxane (PDMS), quartz, glass, silicon, etc. are used as a material for the microchip. The microchip made from PDMS is used as a disposable chip and the manufacturing costs are low. On the contrary, the microchips made from quartz, glass, silicon, etc. are possible to be used repeatedly since they are manufactured by dry and wet etching and bonding, which require high process costs.

In case the microchip is made from quartz or glass, a UV detector can be introduced in order to analyze the samples. FIG. 1 depicts an electrophoresis system equipped with the UV detector introduced thereto. The UV detector has relatively low costs and can be conveniently operated compared to any other detector such as a fluorescence detector. In addition, since signals are received from the entire channel region by means of zone detection, transports of the samples to be analyzed in the channel can be observed in real time. In such an electrophoresis system with the UV detector, in order to enhance a peak intensity (i.e., a signal-to-noise ratio (S/N ratio) of UV light), a technology for manufacturing a microchip, which allows the incident UV light to focus on only the channel and the stray light to cut off except the channel region, is necessary.

As a current technical state relevant to such a technology, the following papers disclose microchips, wherein an optical slit made of Si/SiO$_2$ is provided between the channel plate and the reservoir plate: a paper entitled "Single-step quantitation of DNA in microchip electrophoresis with linear imaging UV detection and fluorescence detection through comigration with a digest" (F. Xu et al.) published in the *Journal of Chromatography A*, vol. 1051, pp. 147-153, 2004; a paper entitled "High-speed electrophoretic analysis of 1-phenyl-3-methyl-5-pyrazolone derivatives of monosaccharides on a quartz microchip with whole-channel UV detection" (S. Suzuki et al.) published in the *Electrophoresis*, vol. 24, pp. 3828-3833, 2003; a paper entitled "Fabrication of quartz microchip with optical slit and development of a linear imaging UV detector for microchip electrophoresis systems" (H. Nakanishi et al.) published in the *Electrophoresis*, vol. 22, pp. 230-234, 2001; a paper entitled "Studies on SiO$_2$—SiO$_2$ bonding with hydrofluoric acid. Room temperature and low stress bonding technique for MEMS" (H. Nakanishi et al.) published in the *Sensors and Actuators*, vol. 79, pp. 237-244, 2000. Those microchips have been developed to be limited to only quartz material and are being marketed by Shimadzu Instruments (Kyoto, Japan).

However, quartz material is expensive. In addition, both dry etching and wet etching are required in order to form the channels on the channel plate made from quartz. Therefore, there is a problem with the microchip made from quartz in that its material is expensive and its process and manufacturing costs are high. Because wet etching is apt to render the cross-sectional shape of the channel isotropic while causing undercuts in the channel, the channel of the microchip formed by wet etching is further or less etched than the desired depth and width. There is another problem with the microchip made from quartz in that it is difficult to bond the channel plate and the reservoir plate during manufacturing the microchip.

Accordingly, there is a need to provide an electrophoresis microchip made from a more inexpensive material than quartz (e.g., glass) to reduce operation costs and to facilitate microchip supply. Further, there is a need to provide an electrophoresis microchip, wherein its channels are formed by dry etching instead of wet etching in order to render the cross-sectional shape of the channel anisotropic and to reduce process costs. Furthermore, there is a need to provide an electrophoresis microchip, which is configured such that a channel plate and a reservoir plate are easily bonded.

BRIEF DESCRIPTION OF THE DRAWINGS

Arrangements and embodiments may be described in detail with reference to the following drawings in which like reference numerals refer to like elements and wherein.

DETAILED DESCRIPTION OF THE PRESENT INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
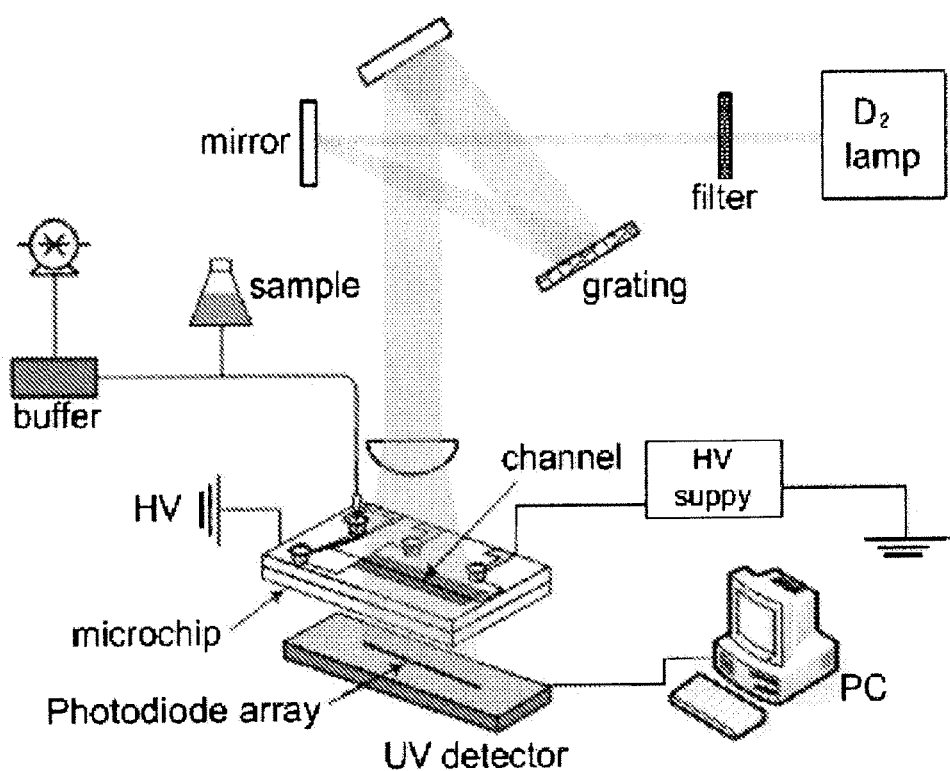
FIG. 1 depicts an electrophoresis system.
Figure 2:
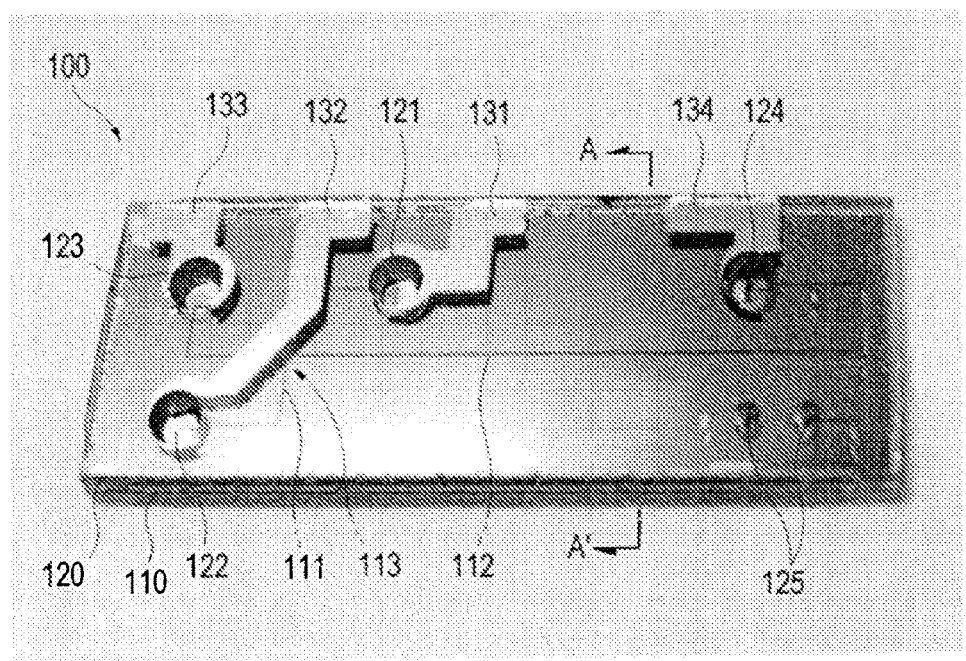
FIG. 2 is a photograph showing an electrophoresis microchip according to the present invention.

FIG. 2 is a photograph showing an embodiment of a microchip constructed according to the present invention. The microchip 100 of this embodiment is sized to be 3.5 cm long and 1.25 cm wide.

The microchip 100 comprises a channel plate 110, a reservoir plate 120, electrodes for sample 131 and 132 and electrodes for buffer 133 and 134. The channel plate 110 is formed with a loading channel 111 (into and out of which a sample solution flows) and a separation channel 112 (into and out of which a buffer solution flows). The reservoir plate 120 is bonded to an upper side of the channel plate 110. The reservoir plate 120 has a sample inlet reservoir 121 and a sample outlet reservoir 122, which are in communication with both ends of the loading channel 111. The reservoir plate 120 also has a buffer inlet reservoir 123 and a buffer outlet reservoir 124, which are in communication with both ends of the separation channel 112, as well as align mark holes 125. The sample inlet reservoir 121 and outlet reservoir 122, the buffer inlet reservoir 123 and outlet reservoir 124, and the align mark holes 125 are formed at the reservoir plate 120. The electrodes for sample 131 and 132 are formed to extend from an upper surface of the reservoir plate 120 to the inlet reservoir 121 and the outlet reservoir 122, respectively. The electrodes for buffer 133 and 134 are formed to extend from an upper surface of the reservoir plate 120 to the inlet reservoir 123 and the outlet reservoir 124, respectively. Between an upper surface of the channel plate 110 and a lower surface of the reservoir plate 120, there is provided an optical slit layer, which is composed of silicon, except the region of the channels 111 and 121. Said optical slit layer is accordingly formed on the channel plate 110.

The channel plate 110 is fabricated from a Silicon On Glass wafer (SOG wafer). The channels 111 and 112 are formed by dry etching (e.g., deep reactive ion etching) on a surface of the SOG wafer in accordance with patterns of the channels. The reservoir plate 120 is fabricated from a glass wafer by drilling (e.g., sand blasting) the glass wafer in accordance with patterns of the inlet reservoirs 121 and 123, the outlet reservoirs 122 and 124, and the align mark holes 125. An upper surface of said optical slit layer, which is provided between the channel plate 110 and the reservoir plate 120, and the lower surface of the reservoir plate 120 are anodic bonded to each other. The electrodes 131, 132, 133 and 134 are formed by sputtering Pt.

The sample solution flows into the loading channel 111 from the inlet reservoir 121 and passes through the loading channel 111 and then flows out from the outlet reservoir 122. The buffer solution flows into the separation channel 112 from the inlet reservoir 123 and passes through separation channel 112 and then flows out from the outlet reservoir 124. While the sample solution flows from the inlet reservoir 121 to the outlet reservoir 122, a certain amount of sample solution is positioned at an intersection 113 of the channels 111 and 112 by an electric field applied by the electrodes 131 and 132. Particles in the sample solution located at the intersection 113 are moved into the separation channel 112 according to their own mobility by an electric field applied by the electrodes 133 and 134 to be thereby separated from the sample solution. Based on such electrophoretic phenomenon, the particles in the sample solution can be analyzed by irradiating UV light into the separation channel 112 and detecting the same.

The microchip 100, which is shown in FIG. 2, can be obtained by cutting bonded wafer, which is formed with a plurality of microchips, by using the Nd:YAG laser.

MEMS fabrication for manufacturing the glass microchip 100 for electrophoresis of the present invention will now be described with reference to FIGS. 3 and 10.

Figure 3:
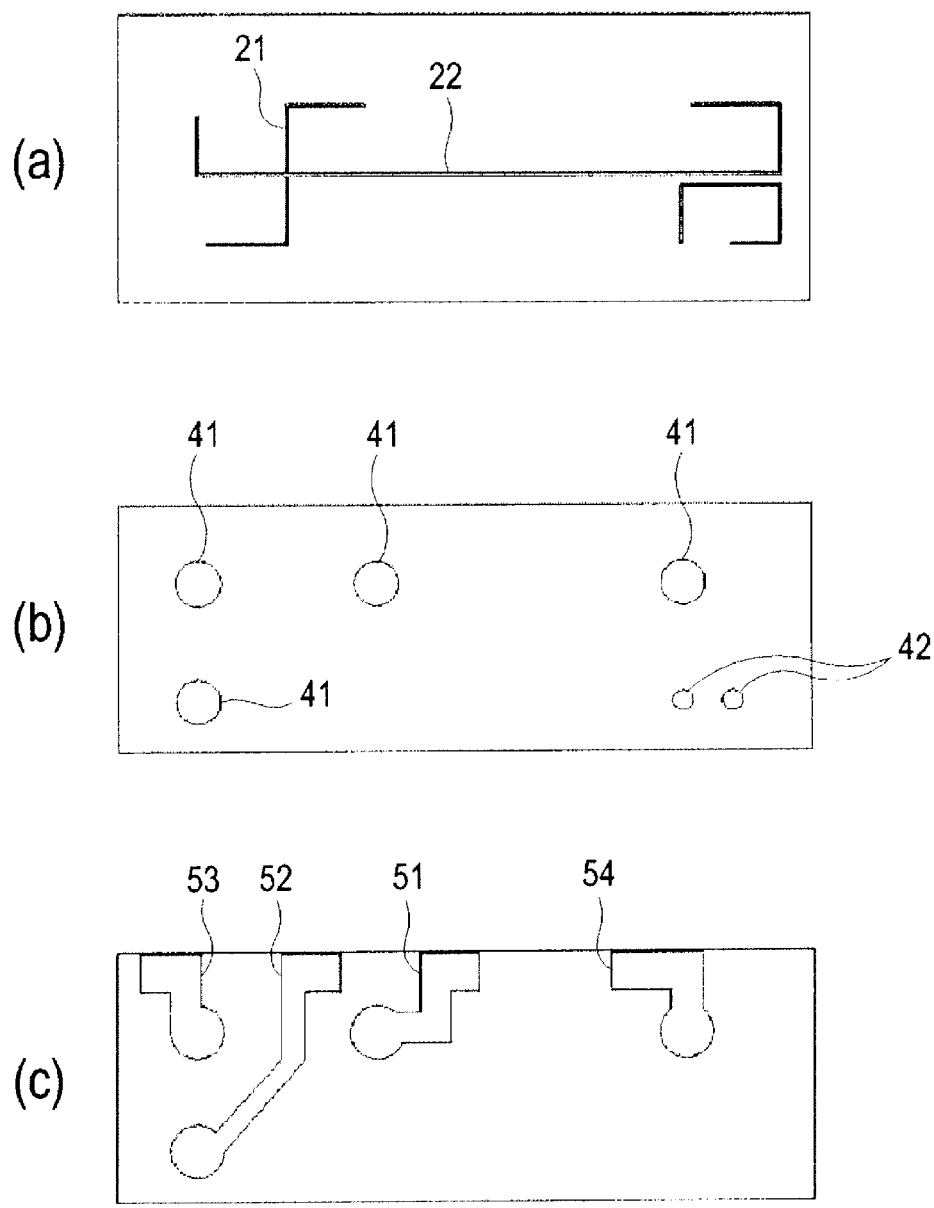
FIG. 3 shows design diagrams of masks required to manufacture the microchip according to the present invention.

FIG. 3 shows design diagrams of masks required to manufacture the microchip of the present invention. FIG. 3(a) is a design diagram of a mask for channel-patterning. The mask for channel-patterning comprises a plurality of units shown in FIG. 3(a). An individual microchip is sized to be 3.5 cm long and 1.25 cm wide. Each unit is formed with slits 21 and 22 of 110 μm width for pattering the loading channel 111 and the separation channel 112. FIG. 3(b) is a design diagram of a mask for reservoir-patterning. The mask for reservoir-patterning comprises a plurality of units shown in FIG. 3(b). Each unit is formed with four holes 41 of 2.23 mm diameter for patterning the sample inlet reservoir and outlet 121 and 122 and the buffer inlet reservoir and outlet 123 and 124 and two holes 42 of 1.0 mm diameter for patterning the align mark hole 125. Both the mask for channel-pattering and the mask for reservoir-patterning are prepared as a film mask so as to be applicable to photolithography. FIG. 3(c) is a design diagram of a mask for electrode-deposit. The mask for electrode-depositing comprises a plurality of units shown in FIG. 3(c). Each unit is formed with holes 51, 52, 53 and 54, which correspond to the shapes of the electrodes for sample 131 and 132 and the electrodes for buffer 133 and 134, respectively.

Figure 4:
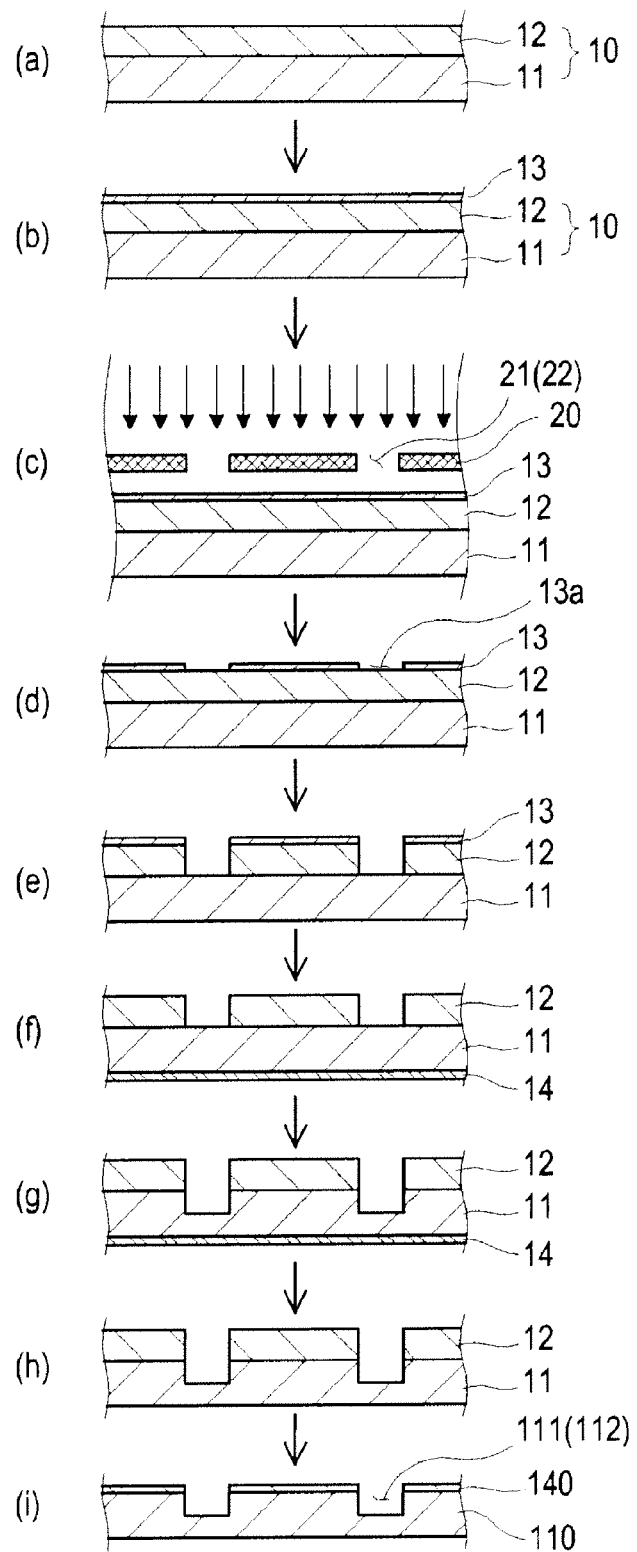
FIG. 4 shows a manufacturing process of a channel plate.

FIG. 4 shows a manufacturing process of a channel plate.

In order to manufacture the channel plate 110, as shown in FIG. 4(a), a Silicon On Glass (SOG) wafer 10 of 4 inch diameter is prepared. In this embodiment, a SOG wafer having a silicon layer 12 of 50 μm thickness and a glass layer 11 of 500 μm thickness is selected as the SOG wafer 10. The prepared SOG wafer 10 is immersed in Piranha solution ($H_2SO_4:H_2O=1:3$) for about 10 minutes. Thereafter, the SOG wafer is cleaned in deionized water using $N_2$ bubbles.

As shown in FIG. 4(b), a photo resist (PR) layer 13 is formed on a surface of the silicon layer 12 of the cleaned SOG wafer 10. Preferably, in order to enhance the adhesiveness of the PR layer 13 on the silicon layer 12, moisture on the surface of the SOG wafer 10 is removed and hexamethyldisilazane (HMDS) is applied thereon, rendering the surface of the silicon layer 12 hydrophilic. Since the silicon layer is always covered with a thin native oxide of 20-50 Å, when it reacts together with HMDS, a strong bonding is obtained therebetween. The PR layer 13 is formed with a thickness of 10 μm by spinning the SOG wafer 10 at 2000 rpm. Thereafter, soft baking is carried out at 110° C. for 2.5 minutes by a hot plate.

Next, patterning for forming the loading channel 111 and the separation channel 112 is carried out on the PR layer 13 of the SOG wafer 10. Said pattering is carried out with a photo-lithography method.

More specifically, as shown in FIG. 4(c), the PR layer 13 is exposed to UV light with an intensity of 34 mW/cm$^2$ using the film mask 20 for channel-patterning and a mask aligner. The part of the PR layer 13, which is exposed to the UV light passing through the slits 21 and 22 of the film mask 20, is modified by such exposure. Accordingly, the PR layer 13 is formed with the same pattern as the slits formed in the film mask 20. Next, as shown in FIG. 4(d), if developed by a developer (e.g., MIF 400K) and cleaned in deionized water, then the part, which is modified and patterned, is separated from the PR layer 13 and a desired channel 13a is thus formed in the PR layer 13. In such a case, the formed channel 13a is sized to be of about 110 μm width and of about 10 μm depth. When the channel development is ascertained with the aimed width and depth by using a microscope and a profilometer, the SOG wafer 10 is hard baked at 130° for 3 minutes.

Next, as shown in FIG. 4(e), the silicon layer 12 is etched by deep reactive ion etching (DRIE). DRIE can etch by a thickness of thousands Å to several μm by destroying molecular bonds by means of continuous collision and acceleration caused by electrical attraction of the ions created within a vacuum environment and radicals. In this embodiment, the DRIE process of the silicon layer 12 is carried out by supplying $SF_6/O_2$ (etching gas) at 160/16 sccm and $C_4F_8$ (passivating gas) at 120 sccm under a switching condition of 100 mTorr pressures and 10 minutes. Since the PR layer 13 is formed on the silicon layer 12, the silicon layer 12 is etched by DRIE in accordance with the channel pattern 13a formed in the PR layer 13.

The etched portion does not become completely anisotropic, because physical and chemical etching may simultaneously occur in RIE. As pressure is lower and energy is higher, the mean free paths of the reacting molecules become gradually longer than the etched depth and activated particles actively collide against a bottom surface. Thus, the anisotropy of the etched portion is enhanced. If DRIE of the silicon layer 12 is ended, then the SOG wafer 10 is cleaned in deionized water.

Next, as shown in FIG. 4(f), the SOG wafer is immersed in acetone solution for 3 minutes, thereby stripping the PR layer 13. In addition, as a preprocess for DRIE of the glass layer 11, an aluminum layer 14 is deposited on a back surface of the SOG wafer 10. Depositing the aluminum layer 14 is carried out by thickness of 1 nm under a condition of 10 kV and 30 mA by means of an E-beam evaporator.

Next, as shown in FIG. 4(g), DRIE for forming the loading channel 111 or the separation channel 112 in the glass layer 11 is performed. DRIE of the glass layer 11 is carried out at 4-10 mTorr and 60° C. using $C_4H_8$ and He gas. $C_4H_8$ etches the glass layer 11 by reaction with the glass layer 11. He gas reduces the isotropy of the channel shape to be etched, establishing a vertical trench. In such a case, since the silicon layer 12, which is located on the glass layer 11, is already etched in accordance with the channel 13a formed in the PR layer 13, the glass layer 11 is formed with the loading channel 111 and the separation channel 112 in accordance with the channel shapes formed in the film mask 20. That is, the silicon layer 12 can play a role as an etch mask during DRIE of the glass layer 11.

After completing DRIE of the glass layer 11, as shown in FIG. 4(h), the SOG wafer 10 is immersed in sulfuric acid solution for 10 minutes, thereby stripping the aluminum layer 14 deposited on the back surface of the SOG wafer 10.

Next, as shown in FIG. 4(i), flattening the surface of the silicon layer 12 is carried out so that a surface roughness of the silicon layer 12 is reduced for subsequent bonding process of the channel plate and the reservoir plate. Flattening the surface is carried out by chemical mechanical polishing (CMP). When flattening the surface is completed, the thickness of the silicon layer 12 of the SOG wafer 10 becomes 10 μm.

The SOG wafer 10, which is fabricated through the above-described processes, becomes the channel plate 110, wherein both the loading channel 111 and the separation channel 112 are formed on its upper surface and the optical slit layer 140 made from silicon is formed thereon except the region of the channels 111 and 112.

Figure 5:
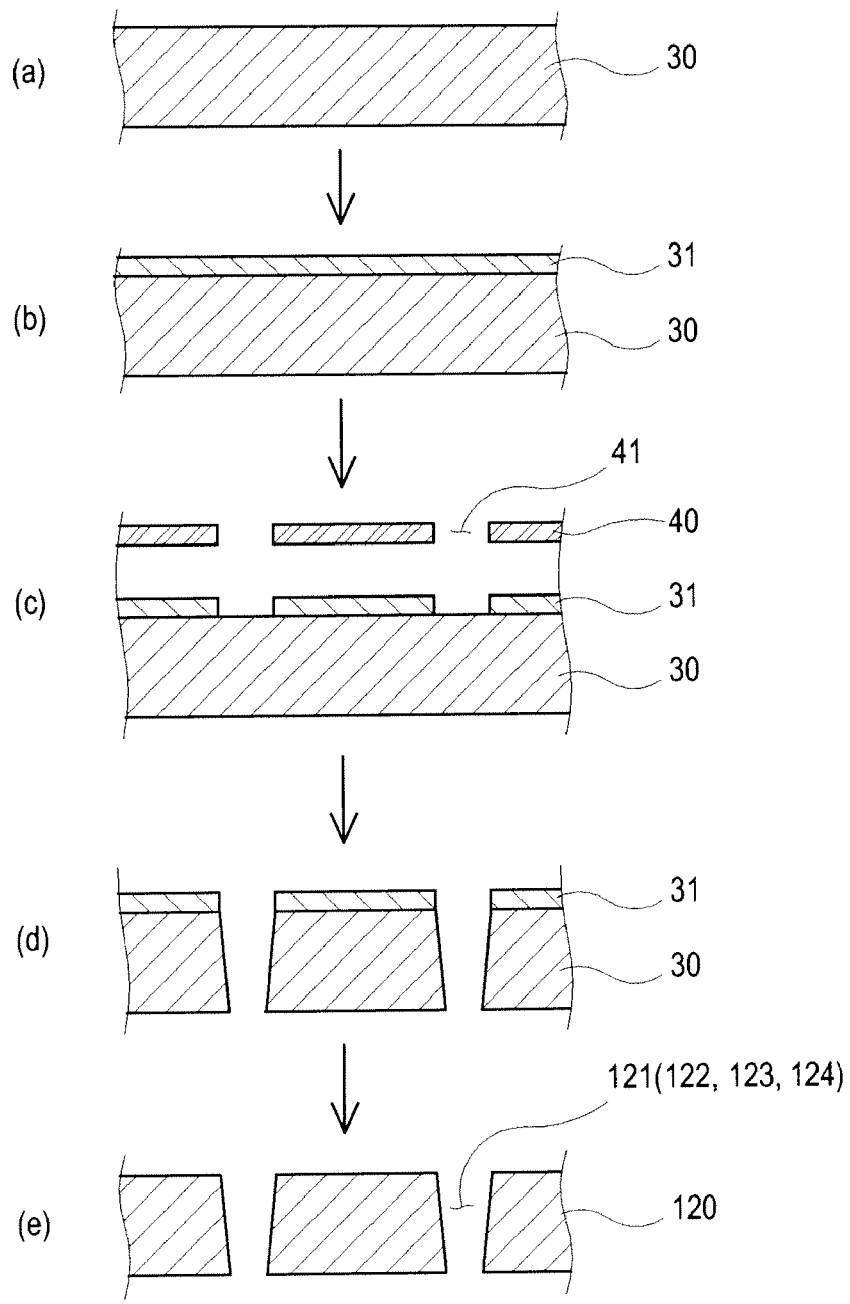
FIG. 5 shows a manufacturing process of a reservoir plate.

FIG. 5 shows a manufacturing process of a reservoir plate.

As shown in FIG. 5(a), in order to manufacture the reservoir plate 120, a glass wafer 30 having a diameter of 4 inches and a thickness of 1 mm is prepared. In this embodiment, a glass wafer based on borosilicate, which has minimal impurities, and both surfaces of which is well polished, is selected as the glass wafer 30 to eliminate any disturbances that occur during electrophoresis detection.

Next, as shown in FIG. 5(b), a dry film resist (DFR) layer 31 is attached on an upper surface of the glass wafer 30.

Thereafter, as shown in FIG. 5(c), patterning the reservoir shapes is carried out with a photolithography method. More specifically, the desired reservoir pattern is formed in the DFR layer 31 by disposing a film mask 40 for reservoir-patterning above the DFR layer 31 and exposing the wafer 30 to UV light and developing and cleaning the wafer 30.

Next, as shown in FIG. 5(d), the glass wafer 30 is formed with holes by sand blasting the wafer 30. Since the DFR layer 31 is formed with the patterns corresponding to the sample inlet reservoir and outlet reservoir, the buffer inlet reservoir and outlet reservoir, and the align mark hole, the glass wafer 30 is formed with the sample inlet reservoir and outlet reservoir, the buffer inlet reservoir and outlet reservoir, and the align mark hole in accordance with the patterns of the DFR layer 31.

Next, as shown in FIG. 5(e), the glass wafer 30 is immersed in acetone solution, thereby stripping the DFR layer 31.

The glass wafer 30, which is fabricated by the above-described processes, becomes the reservoir plate 120, wherein the sample inlet reservoir 121 and outlet reservoir 122, the buffer inlet reservoir 123 and outlet reservoir 124 are drilled therethrough.

Figure 6:
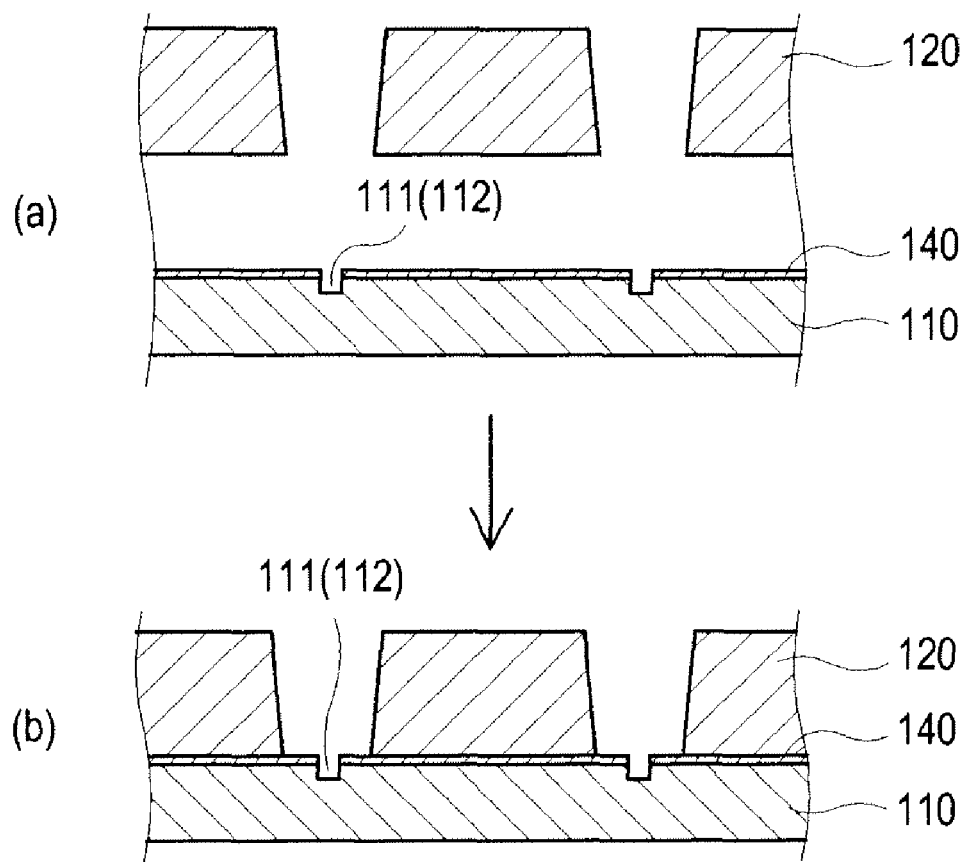
FIG. 6 shows a bonding process of the channel plate and the reservoir plate.

FIG. 6 shows a bonding process of the channel plate and the reservoir plate.

After disposing the reservoir plate 120 above the channel plate 110 as shown in FIG. 6(a), the channel plate 110 and the reservoir plate 120 are bonded to each other. The microchip 100 of the present invention is fabricated by anodic bonding both of the plates 110 and 120.

For anodic bonding, a wafer bonder is utilized and a hot plate is heated to 360° C. Further, the optical slit layer 140 made from silicon is connected to an anode and the reservoir plate 120 is connected to a cathode. A voltage of 800V is applied by a direct current power supply while a pressure of 3 kg/cm$^2$ is applied to both of the plates 110 and 120 for 30 minutes. Then, (+) ions, which exist on the surface of the optical slit layer 140 made from silicon, are bonded to oxygen ions (−) of the reservoir plate 120 (i.e., the glass wafer 30), thereby accomplishing anodic bonding.

Figure 7:
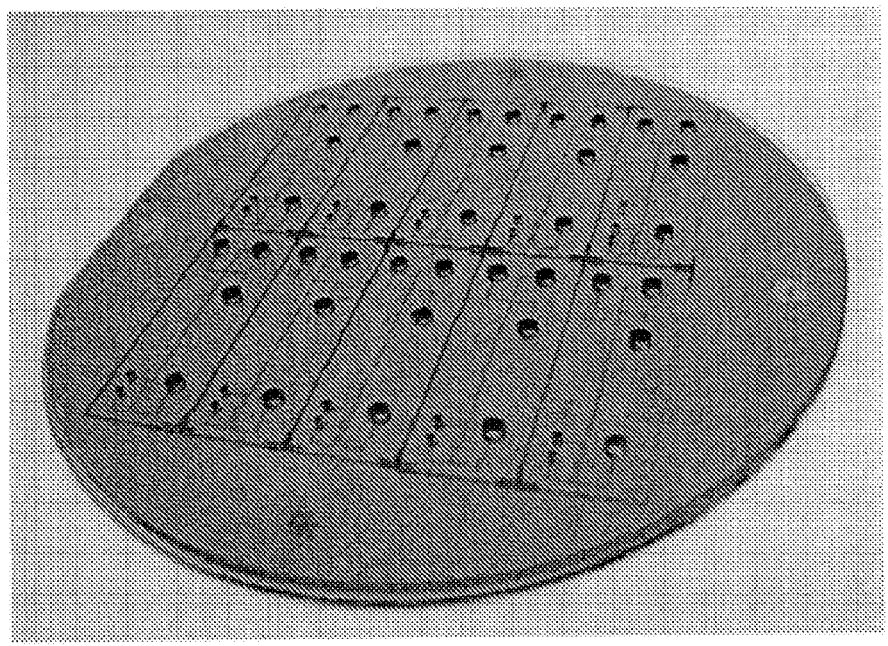
FIG. 7 is a photograph showing a bonded wafer of the channel plate and the reservoir plate, which is bonded to each other by anodic bonding.

Anodic bonding utilizes movements of Na ions and Li ions contained in glass. If a temperature is raised, then Na ions are moved to the cathode and bonding is carried out. When Na ions are moved, space charge is created and potential drop occurs at an interface of the reservoir plate 120 made from glass and the optical slit layer 140 made from silicon. High electrical field between the glass and silicon layer causes an electrostatic force and covalent bond is made thereby. According to the inventor's experiment, a pin-hole phenomenon, which may occur in incomplete bonding, does not occur between the anodic bonded plates 110 and 120. FIG. 7 is a photograph showing a bonded wafer of the channel plate and the reservoir plate by anodic bonding.

Figure 8:
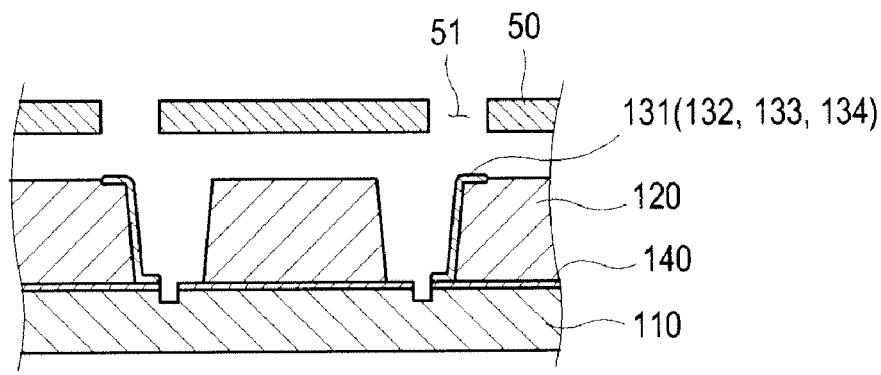
FIG. 8 shows an electrode deposition process.
Figure 9:
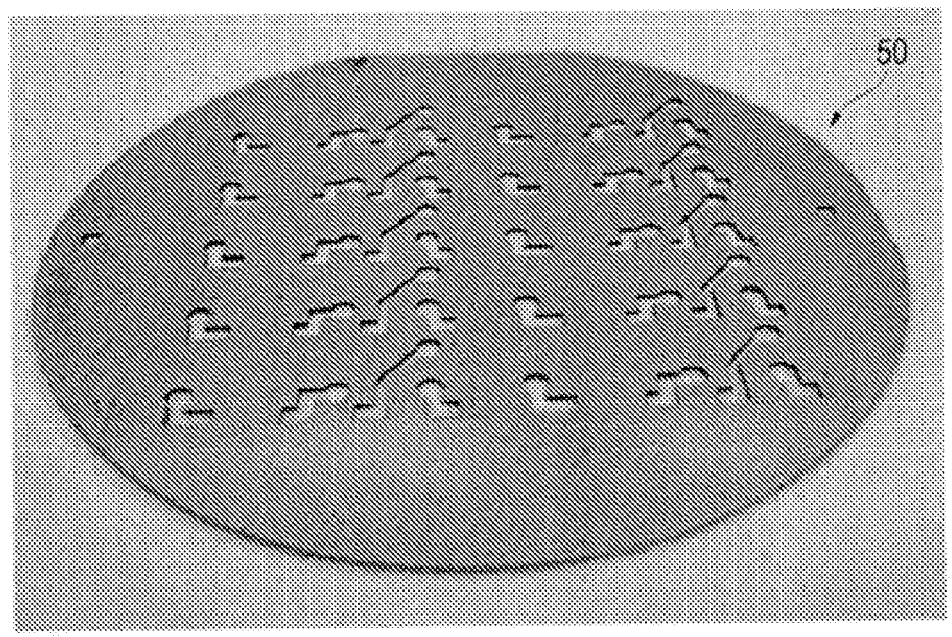
FIG. 9 is a photograph showing a shadow mask for electrode deposition.

FIG. 8 shows an electrode deposition process. FIG. 9 is a photograph showing a shadow mask for electrode deposition.

The electrodes for sample 131 and 132 and the electrodes for buffer 133 and 134 are formed as shown in FIG. 8. The electrodes 131, 132, 133 and 134 are formed as a thin layer comprised of Pt and Ti by sputtering.

A mask 50 shown in FIG. 9 is a shadow mask fabricated for the purpose of depositing the electrodes. A silicon wafer having a diameter of 4 inches is prepared as a shadow mask 50. The shadow mask 50 for electrode depositing is fabricated by drilling the holes, through which an electrode material passes during sputtering, in the prepared silicon wafer by means of the Nd:YAG laser.

As shown in FIG. 8, the electrodes are deposited by sputtering in a state where the shadow mask 50 is disposed above the bonded plates 110 and 120.

Direct current sputtering is used in this embodiment. Since an amount of electric current is nearly proportional to a thickness of the thin layer in direct current sputtering, the deposited thin layer is highly uniform and the intensity of sputtering is high.

In the sputtering process of the present invention, a target material (Pt/Ti) is set as cathode, the bonded plates are set as anode, and Ar gas is used for creating ions. The shadow mask 50 is disposed above the bonded wafer and an internal pressure of a sputtering chamber is set to 7 mTorr and Ar gas is injected thereinto. Further, a direct current power source of 100 W is applied. Then the injected Ar gas is ionized. Specifically, Ar emits energy while emitting an electron and the $Ar^+$ ions in the plasma environment are accelerated by electric potential difference with collision against a surface of a target material, thereby forming the thin layer. In order to enhance the effectiveness of sputtering Pt, Ti is first sputtered by a thickness of 20 nm at a room temperature and then Pt is sputtered by a thickness of 500 nm.

Figure 10:
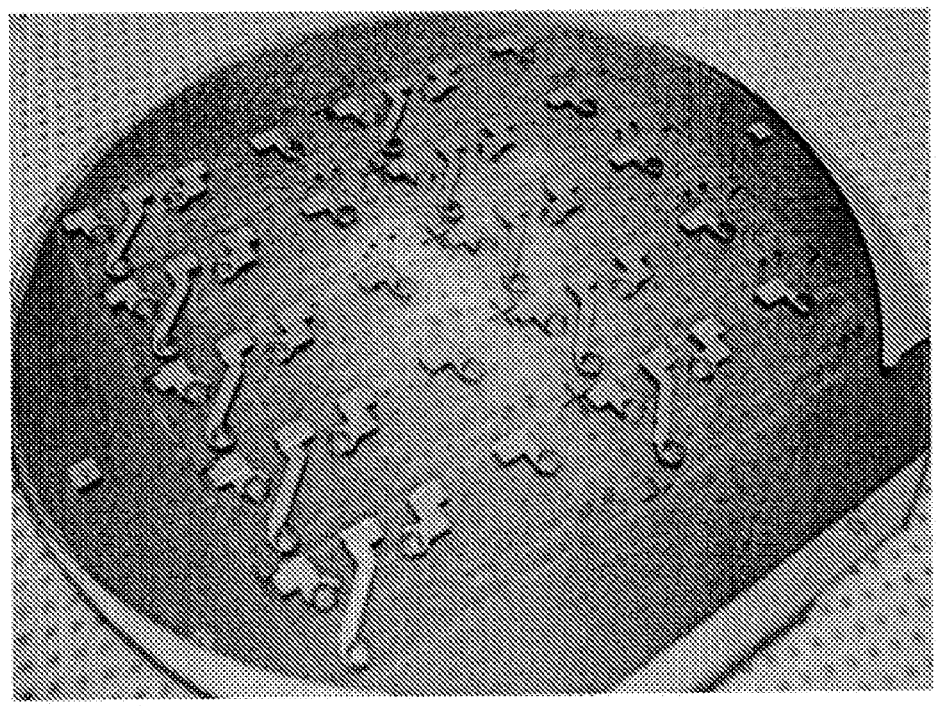
FIG. 10 is a photograph showing the bonded wafer with the electrodes deposited thereon.

The bonded wafer with the electrodes deposited thereon is fabricated by the above-described processes, as shown in FIG. 10. The bonded wafer is prepared with a plurality of microchips (in this embodiment, ten microchips). The microchip 100 shown in FIG. 2 is fabricated by cutting the completed bonded wafer by means of the Nd:YAG laser. The completed microchip 100 is formed with the sample inlet reservoir 121 and the sample outlet reservoir 122 and the buffer inlet reservoir 123 and the buffer outlet reservoir 124. Further, the completed microchip 100 is formed with the loading channel 111, the separation channel 112, and the optical slit layer 140 made of silicon locating between the channel plate 110 and the reservoir plate 120 except the region of the channels 111 and 112.

Figure 11:
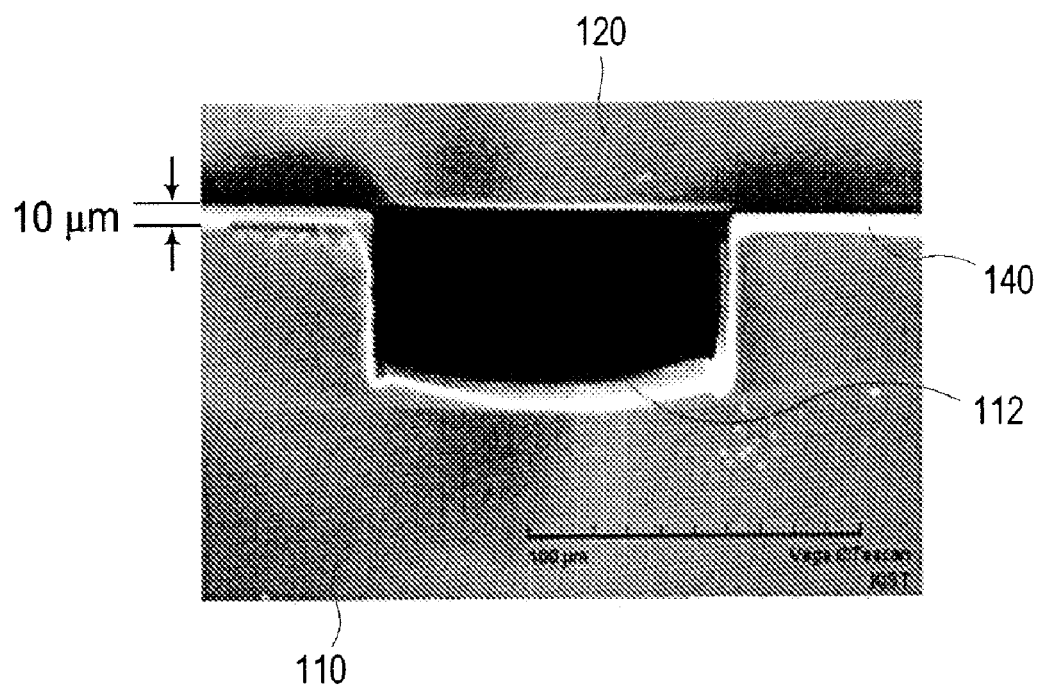
FIG. 11 is a photograph taken with a scanning electron microscope, which shows a cross-section of a channel taken along the line A-A' of FIG. 2.

FIG. 11 is a photograph of a cross-section of the microchip taken along the A-A line of FIG. 2, which was actually manufactured by the above-described processes. It was taken with a field emission scanning electron microscope (Hitachi: S-4700). The characteristics of the channel provided in the microchip become a factor having an important effect on the performance of the electrophoresis, by which a small amount of samples must be analyzed. As can be seen from FIG. 11, the channel 112 of the finished microchip 100 has a rectangular cross-section. That is, an anisotropic cross-section was obtained. The measured channel is 107 μm wide at its top and is 45 μm deep. It is estimated that a bottom surface of the channel is not even since an incomplete etching occurred due to the impurities contained in glass. Further, it can be clearly seen that the optical slit layer 140 made from silicon was formed between the channel plate 110 and the reservoir plate 120 by a thickness of 10 μm from FIG. 11. As such, since the channel 112 is etched in an anisotropic cross-section by DRIE, the channel can be precisely etched by desired depth and width. Furthermore, since etching can be carried out continuously in one direction (more specifically, continuous etching in a depth direction of the channel) by dry etching such as DRIE, a so-called high-aspect-ratio channel can be formed. Due to the optical slit layer, the UV light irradiated to the channel can be detected in the state where it focuses on only the channel and the stray light cuts off except the channel region. Further, the UV light having passed through the channel does not undergo a refraction phenomenon, thereby enhancing detection efficiency.

Figure 12:
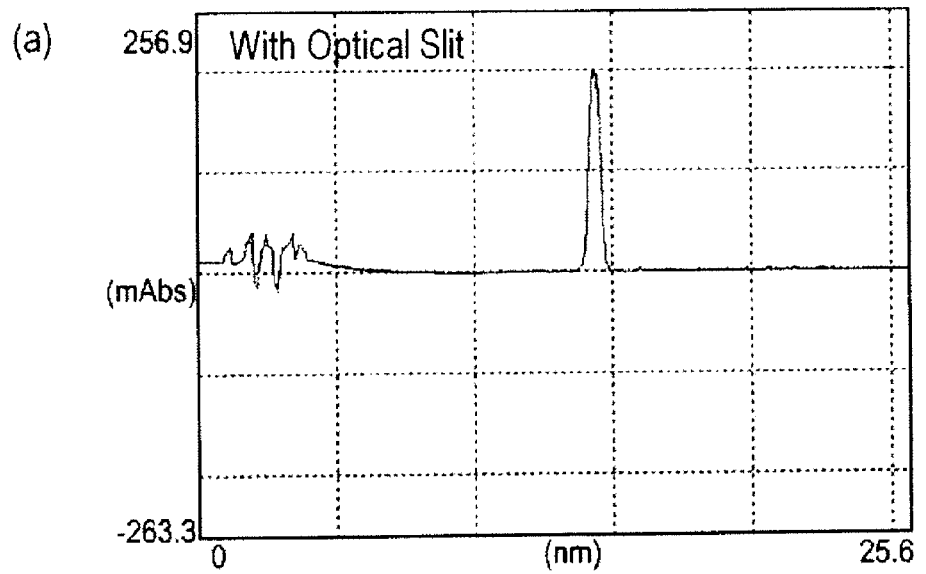
FIG. 12(a) shows an electropherogram and a gel image of electroosmotic flow velocity of a benzyl alcohol marker, which is measured by the microchip of the present invention.
FIG. 12(b) shows an electropherogram and a gel image of electoosmotic flow velocity of a benzyl alcohol marker, which is measured by any other microchip without an optical slit.
Figure 12:
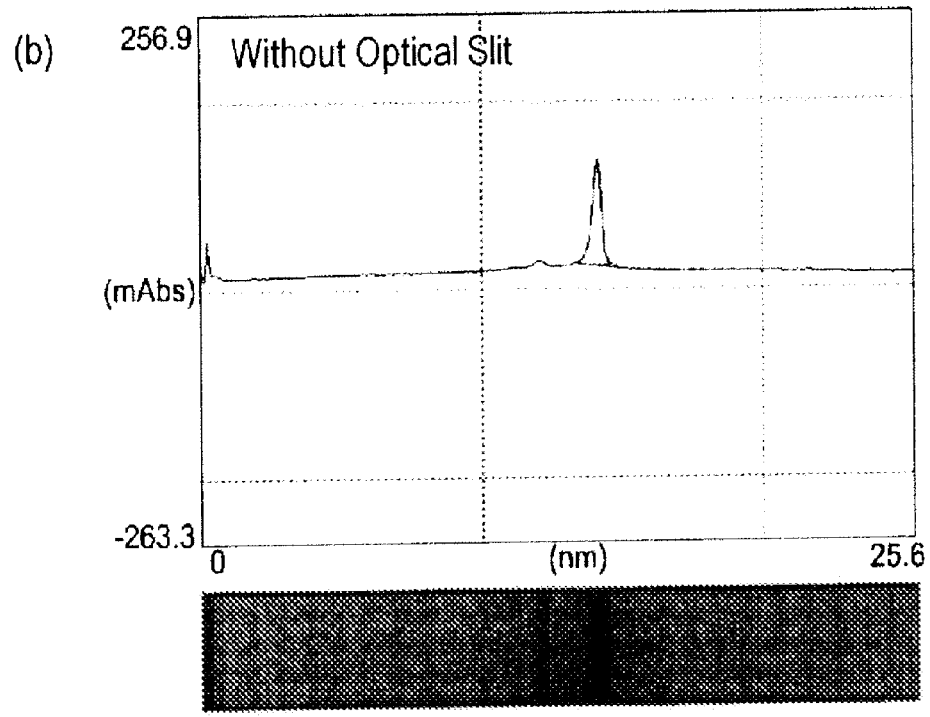

The present inventor conducted an experiment, wherein it can be ascertained that the glass microchip obtained by the above-described fabricating process has the performance suitable for the electrophoresis. The experiment was conducted by measuring an electroosmotic flow velocity of a neutral marker. The experiment was also conducted on a glass microchip with an optical slit layer such as the microchip of the present invention and other glass microchip without an optical slit layer. Microchip electrophoresis equipment used for measurement was "MCE2010" (Shimadzu Corp., Japan). 50 mM Tris of pH10.7 was used as buffer solution. Benzyl alcohol was used as the neutral marker. An electric field of 500V and 5-10 μA was applied. According to the experiment, the electroosmotic flow velocity was measured as 0.36 mm/s. FIG. 12(a) shows an electrophoresis peak (i.e., electropherogram) and a gel image of the electoosmotic flow velocity of the benzyl alcohol marker, which is measured using the microchip of the present invention. FIG. 12(b) shows an electrophoresis peak and a gel image of the electoosmotic flow velocity of the benzyl alcohol marker, which is measured using any other microchip without an optical slit layer. As shown in the electropherograms of FIGS. 12(a) and 12(b), the S/N ratio and the UV absorbance of the case with the optical slit layer made from silicon (e.g., FIG. 12(a)) was superior to those of the case without the optical slit layer (e.g., FIG. 12(b)). The peak properties of the glass microchips are comparatively shown in below Table 1 according to whether the microchip has or does not have the optical slit layer made from silicon. As can be seen from Table 1, in the case with the optical slit layer, the S/N ratio is enhanced about 3 times and the maximum UV absorbance is enhanced about 1.7 times. Meanwhile, as measured using a quartz microchip with an optical slit layer made from $Si/SiO_2$ (its channels are 110 μm wide and 50 μm deep), which can be available from Shimadzu Instruments (Japan), its electoosmotic flow velocity was 0.5 mm/s and its maximum UV absorbance was 295±5 mAbs. The quartz microchip was superior to the glass microchip in view of the electoosmotic flow velocity and the maximum UV absorbance. However, the S/N ratio was shown to be nearly similar in both cases.

TABLE 1

| Peak Properties | Without optical slit | With optical slit |
|---|---|---|
| S/N Ratio | 5.5-6.6 | 14-23 |
| Max. UV Absorbance(mAbs) | 118 ± 5 | 195 ± 5 |

Embodiments of the present invention may provide a glass electrophoresis microchip with an optical slit layer, which is applicable to an electrophoresis employing UV detection. Further, embodiments of the present invention may provide a method of manufacturing such a microchip by MEMS fabrication. Since the microchip is made from glass, manufacturing costs are reduced compared to the prior art quartz microchip. Further, since the channels are formed by only the DRIE process instead of a wet etching process, the manufacturing time for the microchip can be shortened and the process costs can also be reduced. Furthermore, since the cross-sectional shape of the channel becomes anisotropic by the dry etching of DRIE, the channel having a desired size can be precisely etched. The silicon layer interposed between the channel plate and the reservoir plate serves as an optical slit layer capable of enhancing the S/N ratio and the absorbance of UV light. In addition, both the channel plate and the reservoir plate can be easily anodic bonded due to the silicon layer. The microchip constructed in accordance with the present invention can be utilized very usefully in electrophoresis experimentation, wherein many microchips are frequently used due to a great quantity of samples to be analyzed. Moreover, it motivates a μTAS study based on electrophoresis, thereby greatly advancing a bioMEMS technology.

A method of manufacturing an electrophoresis microchip may be provided. The method of the present invention may comprise the following steps: manufacturing a channel plate; manufacturing a reservoir plate; combining the channel plate and the reservoir plate; and forming electrodes. Manufacturing a channel plate may comprise: patterning a channel shape on a silicon layer of a silicon on glass wafer; dry etching the silicon on glass wafer to form channels reaching a glass layer through the silicon layer of the silicon on glass wafer; and flattening a surface of the silicon layer. Manufacturing a reservoir plate may comprise: patterning a reservoir shape on a surface of a glass wafer; and forming reservoirs by drilling through the glass wafer. Combining the channel plate and the reservoir plate may comprise anodic bonding the channel plate and the reservoir plate after disposing the reservoir plate on the silicon layer of the channel plate. Forming electrodes may comprise forming electrodes extending from the reservoir plate to the reservoirs.

Patterning a channel shape during fabrication of the channel plate may comprise: forming a photo resist layer on the silicon layer; disposing a mask having the channel shape over the silicon on glass wafer and exposing the silicon on glass wafer to UV light; developing; and cleaning the silicon on glass wafer in deionized water. Manufacturing a channel plate may further comprise stripping the photo resist layer after dry etching.

Dry etching of manufacturing a channel plate may comprise deep reactive ion etching (DRIE) the silicon layer and deep reactive ion etching (DRIE) the glass layer. Deep reactive ion etching the silicon layer may utilize $SF_6/O_6$ as an etching gas and $C_4F_8$ as a passivating gas. Deep reactive ion etching the glass layer may utilize $C_4H_8$ as a reaction gas and He in order to obtain a vertical trench in the channel.

Pattering a reservoir shape during fabrication of the reservoir plate may comprise: applying a dry film resist layer on the glass wafer; disposing a mask having the reservoir shape drilled therethrough over the glass wafer and exposing the glass wafer to UV light; developing; and cleaning the silicon on glass wafer in deionized water. Forming reservoirs may comprise sand blasting the glass wafer. Manufacturing a reservoir plate may comprise stripping the dry film resist layer after sand blasting.

Combining the channel plate and the reservoir plate may comprise anodic bonding, which is carried out in the state where the silicon layer is connected to an anode and the reservoir plate is connected to a cathode and a direct current power source is applied.

Forming electrodes may comprise sputtering a target material in a condition where both the channel plate and the reservoir plate combined to each other are set as an anode and the target material constituting the electrodes is set as a cathode and a mask with a shape of the electrodes drilled therethrough is disposed above the reservoir plate.

An electrophoresis microchip may also be provided. The microchip may comprise the following: a channel plate formed on a upper surface thereof with a loading channel and a separation channel crossed to the loading channel, the channel plate being composed of glass; an optical slit layer disposed on the upper surface of the channel plate except the channel region, the optical slit layer being composed of silicon; a reservoir plate disposed on the optical slit layer and having a sample inlet reservoir and a sample outlet reservoir and a buffer inlet reservoir and a buffer outlet reservoir drilling therethrough, the sample inlet reservoir and outlet reservoir being in communication with one end and the other end of the loading channel respectively, the buffer inlet reservoir and outlet reservoir being in communication with one end and the other end of the separation channel, the reservoir plate being composed of glass; and electrodes for sample extending from the upper surface of the reservoir plate to the sample inlet reservoir and the sample outlet reservoir respectively and electrodes for buffer extending from the upper surface of the reservoir plate to the buffer inlet reservoir and the buffer outlet reservoir respectively.

The channels may be formed by dry etching the channel plate. The channels may have a rectangular cross-section.

The optical slit layer may accordingly be formed on the channel plate. The optical slit layer and the reservoir plate may be bonded to each other by anodic bonding.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of manufacturing an electrophoresis microchip, comprising:

(a) manufacturing a channel plate from a silicon on glass wafer having a glass layer and a silicon layer, comprising:

patterning a channel shape on the silicon layer of the silicon on glass wafer;

deep reactive ion etching the silicon layer of the silicon on glass wafer in accordance with the channel shape;

deep reactive ion etching the glass layer of the silicon on glass wafer in accordance with the channel shape; and flattening a surface of the silicon layer;

(b) manufacturing a reservoir plate from a glass wafer, comprising:

patterning a reservoir shape on a surface of the glass wafer; and forming reservoirs by drilling through the glass wafer;

(c) combining the channel plate and the reservoir plate after disposing the reservoir plate on the silicon layer of the channel plate; and (d) forming electrodes extending from the reservoir plate to the reservoirs by sputtering after disposing a mask above the channel plate and the reservoir plate combined to each other, wherein after deep reactive ion etching the silicon layer and the glass layer of the silicon on glass wafer channels are formed in the channel plate and an optical slit layer composed of the silicon layer is formed except a region of the channels, and wherein combining the channel plate and the reservoir plate comprises anodic bonding an upper surface of the optical slit layer and a lower surface of the reservoir plate to each other.

2. The method of claim 1, wherein patterning a channel shape comprises: forming a photo resist layer on the silicon layer; disposing a mask having the channel shape over the silicon on glass wafer and exposing the silicon on glass wafer to UV light; developing; and cleaning the silicon on glass wafer by deionized water, and wherein manufacturing a channel plate further comprises stripping the photo resist layer after dry etching.

3. The method of claim 1, wherein deep reactive ion etching the silicon layer utilizes $SF_6/O_6$ as an etching gas and $C_4F_8$ as a passivating gas.

4. The method of claim 1, wherein deep reactive ion etching the glass layer utilizes $C_4H_8$ as a reaction gas and He in order to obtain a vertical trench in the channel.

5. The method of claim 1, wherein patterning a reservoir shape comprises: applying a dry film resist layer on the glass wafer; disposing a mask having the reservoir shape over the glass wafer and exposing the glass wafer to UV light; developing; and cleaning the silicon on glass wafer by deionized water.

6. The method of claim 5, wherein forming reservoirs comprises sand blasting the glass wafer, and wherein manufacturing a reservoir plate comprises stripping the dry film resist layer after sand blasting.

7. The method of claim 1, wherein anodic bonding is carried out in the state where the silicon layer is connected to an anode and the reservoir plate is connected to a cathode and a direct current power source is applied.

8. The method of claim 1, wherein forming electrodes comprises sputtering a target material in a condition where the channel plate and the reservoir plate combined to each other are set as an anode and the target material constituting the electrodes is set as a cathode and the mask with a shape of the electrodes drilled therethrough is disposed above the reservoir plate.

\* \* \* \* \*